United States Patent
Hall et al.

(10) Patent No.: US 7,723,362 B2
(45) Date of Patent: May 25, 2010

(54) PESTICIDAL HETEROCYCLIC DIHALOALLYL COMPOUNDS

(75) Inventors: Roger Graham Hall, Basel (CH); Stephan Trah, Basel (CH); Werner Zambach, Basel (CH); Juraj Tuleja, Bratislava (SK)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/597,005

(22) PCT Filed: Jan. 7, 2005

(86) PCT No.: PCT/EP2005/000094

§ 371 (c)(1),
(2), (4) Date: Aug. 7, 2007

(87) PCT Pub. No.: WO2005/068445

PCT Pub. Date: Jul. 28, 2005

(65) Prior Publication Data

US 2007/0299064 A1  Dec. 27, 2007

(30) Foreign Application Priority Data

Jan. 8, 2004  (CH) .................................. 00023/04

(51) Int. Cl.
| | |
|---|---|
| C07D 401/12 | (2006.01) |
| C07D 257/04 | (2006.01) |
| A61K 31/4439 | (2006.01) |
| A61K 31/41 | (2006.01) |
| C07D 285/13 | (2006.01) |
| C07D 271/113 | (2006.01) |
| C07D 249/12 | (2006.01) |
| C07D 237/12 | (2006.01) |
| C07D 241/18 | (2006.01) |
| C07D 239/36 | (2006.01) |
| C07D 273/04 | (2006.01) |
| C07D 233/72 | (2006.01) |

(52) U.S. Cl. .................. 514/340; 514/381; 544/241; 544/408; 544/319; 544/68; 548/251; 548/136; 548/144; 548/263.2; 548/316.7

(58) Field of Classification Search ............... 548/251; 514/340, 381; 546/258.4, 268.4
See application file for complete search history.

(56) References Cited

U.S. PATENT DOCUMENTS

| | | | |
|---|---|---|---|
| 2004/0132747 A1* | 7/2004 | Emig et al. ................ 514/256 |
| 2005/0176722 A1* | 8/2005 | Bono et al. ............. 514/252.02 |
| 2007/0161642 A1* | 7/2007 | Nishiyama et al. ..... 514/252.03 |
| 2007/0225333 A1* | 9/2007 | Bryans et al. ............... 514/336 |
| 2007/0254363 A1* | 11/2007 | Chen et al. .................. 435/375 |
| 2007/0255061 A1* | 11/2007 | Wensbo et al. ............ 546/268.4 |
| 2008/0064728 A1* | 3/2008 | Edwards et al. ............. 514/340 |

FOREIGN PATENT DOCUMENTS

| | | |
|---|---|---|
| EP | 0736252 | 10/1996 |
| WO | 97/27173 | 7/1997 |

OTHER PUBLICATIONS

Bahiense, et al., Rev Bras Parasitol Vet.;16 (4):243-5.*
Kim, http://www.agnet.org/library/eb/502a/, downloaded Sep. 3, 2008.*

* cited by examiner

*Primary Examiner*—James O Wilson
*Assistant Examiner*—Cecilia M Jaisle
(74) *Attorney, Agent, or Firm*—William F. Mulholland, II

(57) ABSTRACT

The invention relates to compounds of formula

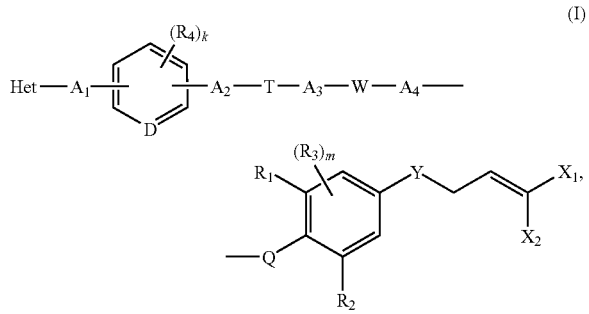

wherein
Het, $A_1$, $A_2$, $A_3$, $A_4$, D, W, T, Q, Y, $X_1$, $X_2$, $R_1$, $R_2$, $R_3$, $R_4$, k and m are as defined hereinabove, and, where applicable, to possible E/Z isomers, mixtures of E/Z isomers and/or tautomers thereof, in each case in free form or in salt form, to a process for the preparation of and to the use of those compounds, E/Z isomers, mixtures of E/Z isomers and/or tautomers, to pesticidal compositions in which the active ingredient has been selected from those compounds, E/Z isomers, mixtures of E/Z isomers and/or tautomers, in each case in free form or in agrochemically usable salt form, to a process for the preparation of and to the use of those compositions, to plant propagation material treated with those compositions, to a method of controlling pests, to intermediates and, where applicable, to possible E/Z isomers, mixtures of E/Z isomers and/or tautomers thereof, in each case in free form or in salt form, for the preparation of those compounds, E/Z isomers, mixtures of E/Z isomers and/or tautomers, and to a process for the preparation of and to the use of those intermediates and, where applicable, possible E/Z isomers, mixtures of E/Z isomers and/or tautomers thereof.

16 Claims, No Drawings

PESTICIDAL HETEROCYCLIC DIHALOALLYL COMPOUNDS

This application is a 371 of International Application No. PCT/EP2005/000094 filed Jan. 7, 2005, which claims priority to CH 00023/04 filed Jan. 8, 2004, the contents of which are incorporated herein by reference.

The invention relates to (1) compounds of formula

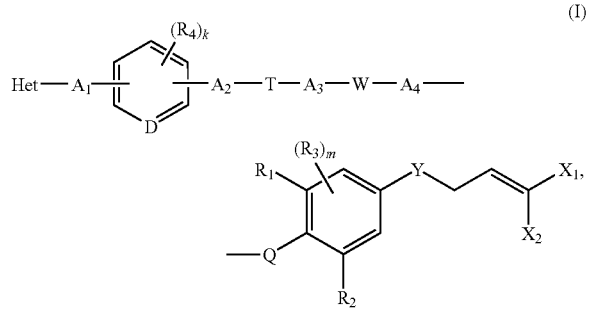

wherein

Het is non-aromatic heterocyclyl that does not contain cumulative double bonds and that has 5 or 6 ring members of which the linking ring member, by way of which Het is linked, by means of a first single bond, to the remainder of the compound of formula I, is either a nitrogen atom that carries two further single bonds which lead to the two ring members of Het directly adjacent to that nitrogen atom, or a carbon atom that carries a further single bond and a double bond which lead to the two ring members of Het directly adjacent to that carbon atom, and the remaining 4 or 5 ring members of Het are, independently of one another, selected from the group consisting of the ring members —C($R_i$)($R_{ii}$)—, —C(=O)—, —C(=S)—, —O—, —S—, —N($R_{iii}$)—, —C($R_{iv}$)= and —N=, wherein (A) of the 5 or 6 ring members of Het, from 1 up to and including 4 ring members, independently of one another, each contributes a hetero atom to the basic ring structure of Het consisting of 5 or 6 ring atoms, (B) two directly adjacent ring members of Het are not both —O—, and (C), when the mentioned linking ring member of Het is a nitrogen atom, either (i) at least one ring member of the mentioned remaining 4 or 5 ring members of Het is —N= or (ii) at least one of the 2 or 3 ring members of Het that are neither the mentioned linking ring member of Het nor its two directly adjacent ring members is —C(=O)— or —C(=S)— or (iii) at least three ring members of the mentioned remaining 4 or 5 ring members of Het are each independently of the others —C($R_{iv}$)= or (iv) at least two ring members of the mentioned remaining 4 or 5 ring members of Het are each independently of the other(s) —O—, —S— or —N($R_{iii}$)— and, when the mentioned linking ring member of Het is a carbon atom, either (v) the mentioned double bond starting from that carbon atom leads to a nitrogen atom or (vi) the ring member of Het bonded to the mentioned further single bond starting from that carbon atom is —C(=O)— or —C(=S)—;

$R_i$ and $R_{ii}$ are each independently of the other hydrogen, halogen, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, $C_2$-$C_6$alkynyl or $C_1$-$C_6$alkoxy-$C_1$-$C_6$alkyl;

$R_{iii}$ is $C_1$-$C_6$alkyl, halo-$C_1$-$C_6$alkyl, $C_1$-$C_6$alkoxy, halo-$C_1$-$C_6$alkoxy, $C_2$-$C_6$alkenyl, $C_2$-$C_6$alkynyl or $C_1$-$C_6$alkoxy-$C_1$-$C_6$alkyl;

$R_{iv}$ is hydrogen, halogen, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, $C_2$-$C_6$alkynyl or $C_1$-$C_6$alkoxy-$C_1$-$C_6$alkyl;

$A_1$, $A_2$ and $A_3$ are each independently of the others a bond or a $C_1$-$C_6$alkylene bridge which is unsubstituted or substituted from one to six times by, each independently of the other(s), $C_3$-$C_8$cycloalkyl, $C_3$-$C_8$cycloalkyl-$C_1$-$C_6$alkyl or halo-$C_1$-$C_3$alkyl;

$A_4$ is a $C_1$-$C_6$alkylene bridge which is unsubstituted or substituted from one to six times by, each independently of the other(s), $C_3$-$C_8$cycloalkyl, $C_3$-$C_8$cycloalkyl-$C_1$-$C_6$alkyl or halo-$C_1$-$C_3$alkyl;

D is CH or N;

W is O, $NR_5$, S, S(=O), S(=O)$_2$, —C(=O)—O—, —O—C(=O)—, —C(=O)—$NR_6$— or —$NR_6$—C(=O)—;

T is a bond, O, NH, $NR_5$, S, S(=O), S(=O)$_2$, —C(=O)—O—, —O—C(=O)—, —C(=O)—$NR_6$— or —$NR_6$—C(=O)—;

Q is O, $NR_5$, S, S(=O) or S(=O)$_2$;

Y is O, $NR_5$, S, S(=O) or S(=O)$_2$;

$X_1$ and $X_2$ are each independently of the other fluorine, chlorine or bromine;

$R_1$ and $R_2$ are each independently of the other H, halogen, CN, nitro, $C_1$-$C_6$alkyl, halo-$C_1$-$C_6$alkyl, $C_1$-$C_6$alkylcarbonyl, $C_2$-$C_6$alkenyl, halo-$C_2$-$C_6$alkenyl, $C_2$-$C_6$alkynyl, $C_1$-$C_6$alkoxy, halo-$C_1$-$C_6$alkoxy, $C_2$-$C_6$alkenyloxy, halo-$C_2$-$C_6$alkenyloxy, $C_3$-$C_6$alkynyloxy, $C_1$-$C_6$alkoxy-carbonyl or halo-$C_3$-$C_6$alkynyloxy;

$R_3$ is halogen, CN, nitro, $C_1$-$C_6$alkyl, halo-$C_1$-$C_6$alkyl, $C_1$-$C_6$alkylcarbonyl, $C_2$-$C_6$alkenyl, halo-$C_2$-$C_6$alkenyl, $C_2$-$C_6$alkynyl, $C_1$-$C_6$alkoxy, halo-$C_1$-$C_6$alkoxy, $C_2$-$C_6$alkenyloxy, halo-$C_2$-$C_6$alkenyloxy, $C_3$-$C_6$alkynyloxy, $C_1$-$C_6$alkoxycarbonyl or halo-$C_3$-$C_6$alkynyloxy, the two $R_3$ substituents being identical or different when m is 2;

$R_4$ is halogen, CN, nitro, $C_1$-$C_6$alkyl, halo-$C_1$-$C_6$alkyl, $C_1$-$C_6$alkylcarbonyl, $C_2$-$C_6$alkenyl, halo-$C_2$-$C_6$alkenyl, $C_2$-$C_6$alkynyl, $C_1$-$C_6$alkoxy, halo-$C_1$-$C_6$alkoxy, $C_2$-$C_6$alkenyloxy, halo-$C_2$-$C_6$alkenyloxy, $C_3$-$C_6$alkynyloxy, $C_1$-$C_6$alkoxycarbonyl or halo-$C_3$-$C_6$alkynyloxy, the $R_4$ substituents being identical or different when k is greater than 1;

$R_5$ is H, $C_1$-$C_6$alkyl, halo-$C_1$-$C_3$alkyl, halo-$C_1$-$C_3$alkylcarbonyl, $C_1$-$C_6$alkoxyalkyl, $C_1$-$C_6$alkylcarbonyl or $C_3$-$C_8$cycloalkyl;

$R_6$ is H, $C_1$-$C_6$alkyl, halo-$C_1$-$C_3$alkyl, halo-$C_1$-$C_3$alkylcarbonyl, $C_1$-$C_6$alkoxyalkyl, $C_1$-$C_6$alkylcarbonyl or $C_3$-$C_8$cycloalkyl;

k is 0, 1, 2 or 3 when D is N or is 0, 1, 2, 3 or 4 when D is CH; and m is 0, 1 or 2, and, where applicable, to possible E/Z isomers, mixtures of E/Z isomers and/or tautomers thereof, in each case in free form or in salt form, to a process for the preparation of and to the use of those compounds, E/Z isomers, mixtures of E/Z isomers and/or tautomers, to pesticidal compositions in which the active ingredient has been selected from those compounds, E/Z isomers, mixtures of E/Z isomers and/or tautomers, in each case in free form or in agrochemically usable salt form, to a process for the preparation of and to the use of those compositions, to plant propagation material treated with those compositions, to a method of controlling pests, to intermediates and, where applicable, to their possible E/Z isomers, mixtures of E/Z isomers and/or tautomers thereof, in each case in free form or in salt form, for the preparation of those compounds, E/Z isomers, mixtures of E/Z isomers and/or tautomers and to a process for the preparation of and to the use of those intermediates and, where applicable, possible E/Z isomers, mixtures of E/Z isomers and/or tautomers thereof.

Certain dihalovinyl derivatives are proposed in the literature as active ingredients in pesticidal compositions. The biological properties of those known compounds in the field of pest control are not, however, entirely satisfactory, and there is accordingly a need to make available further compounds having pesticidal properties, especially for controlling insects and representatives of the order Acarina, that problem being solved in accordance with the invention by provision of the present compounds I.

Compounds I having at least one basic centre are capable, for example, of forming acid addition salts, for example with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted or substituted, e.g. halo-substituted, $C_1$-$C_4$alkanecarboxylic acids, e.g. acetic acid, saturated or unsaturated dicarboxylic acids, e.g. oxalic, malonic, succinic, maleic, fumaric or phthalic acid, hydroxycarboxylic acids, e.g. ascorbic, lactic, malic, tartaric or citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Compounds I having at least one acid group are capable, for example, of forming salts with bases, for example metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally also be formed. In the context of the invention, preference is given to agrochemically advantageous salts, but salts associated with disadvantages in respect of agrochemical applications, for example toxicity to bees or fish, which are used, for example, for the isolation or purification of free compounds I or agrochemically acceptable salts thereof, are also included. In view of the close relationship between the compounds I in free form and in the form of their salts, free compounds I and salts thereof are to be understood hereinabove and hereinbelow as including, where appropriate, both the corresponding salts and the free compounds I, respectively. The same is true correspondingly of tautomers of compounds of formula (I) and salts thereof. In each case the free form is generally preferred.

The general terms used hereinabove and hereinbelow have the following meanings, unless defined otherwise.

Halogen, both as a group per se and as a structural element of other groups and compounds, for example of haloalkyl, halocycloalkyl, haloalkenyl, haloalkynyl and haloalkoxy, is fluorine, chlorine, bromine or iodine, especially fluorine, chlorine or bromine, more especially fluorine or chlorine, very especially chlorine.

Carbon-containing groups and compounds each contain, unless defined otherwise, from 1 up to and including 20, preferably from 1 up to and including 18, more preferably from 1 up to and including 10, especially from 1 up to and including 6, more especially from 1 up to and including 4, even more especially from 1 up to and including 3, yet more especially 1 or 2, carbon atoms, very special preference being given to 1 carbon atom.

Alkylene is a straight-chain or branched bridging member; it is, especially, —$CH_2$—, —$CH_2CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH(CH_3)$—, —$CH(CH_3)$—$CH_2$—, —$CH(C_2H_5)$—, —$C(CH_3)_2$—, —$CH(CH_3)CH_2$—, —$CH(CH_3)CH(CH_3)$— or —$CH_2C(CH_3)_2$—$CH_2$—.

Alkyl, both as a group per se and as a structural element of other groups and compounds, for example of haloalkyl, alkoxy, alkoxyalkyl, haloalkoxy, alkoxycarbonyl, alkylthio, haloalkylthio, alkylsulfonyl and alkylsulfonyloxy, is, in each case taking due account of the particular number of carbon atoms present in the group or compound in question, either straight-chained, e.g. methyl, ethyl, n-propyl, n-butyl, n-hexyl, n-octyl, n-decyl, n-dodecyl, n-hexadecyl or n-octadecyl, or branched, e.g. isopropyl, isobutyl, sec-butyl, tert-butyl, isopentyl, neopentyl or isohexyl.

Alkenyl and alkynyl, both as groups per se and as structural elements of other groups and compounds, for example of haloalkenyl, haloalkynyl, alkenyloxy, haloalkenyloxy, alkynyloxy or haloalkynyloxy, are straight-chained or branched and in each case contain two or, preferably, one unsaturated carbon-carbon bond(s). By way of example there may be mentioned vinyl, prop-2-en-1-yl, 2-methylprop-2-en-1-yl, but-2-en-1-yl, but-3-en-1-yl, prop-2-yn-1-yl, but-2-yn-1-yl and but-3-yn-1-yl.

Cycloalkyl, both as a group per se and as a structural element of other groups and compounds, for example of cycloalkylalkyl, is cyclopropyl, cyclobutyl, cyclopentyl, cyclohexyl, cycloheptyl or cyclooctyl. Preference is given to cyclopropyl, cyclopentyl and cyclohexyl, with special preference being given to cyclopropyl.

Halo-substituted carbon-containing groups and compounds, such as haloalkyl and haloalkoxy, may be partially halogenated or perhalogenated, the halogen substituents in the case of multiple halogenation being identical or different. Examples of haloalkyl, both as a group per se and as a structural element of other groups and compounds, such as of haloalkoxy, are methyl mono- to tri-substituted by fluorine, chlorine and/or bromine, for example $CHF_2$, $CF_3$ or $CH_2Cl$; ethyl mono- to penta-substituted by fluorine, chlorine and/or bromine, for example $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ or $CClFCHClF$; propyl or isopropyl mono- to hepta-substituted by fluorine, chlorine and/or bromine, for example $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl or one of the isomers thereof mono- to nona-substituted by fluorine, chlorine and/or bromine, for example $CF(CF_3)CHFCF_3$, $CF_2(CF_2)_2CF_3$ or $CH_2(CF_2)_2CF_3$.

Preferred embodiments in the context of the invention are
(2) compounds I according to (1) wherein $X_1$ and $X_2$ are chlorine or bromine, especially chlorine;
(3) compounds I according to (1) or (2) wherein $A_1$ is a bond;
(4) compounds I according to (1) to (3) wherein the group $A_2$-T-$A_3$ is a bond;
(5) compounds I according to (1) to (4) wherein W is O, —C(=O)O— or —C(=O)NH—, especially O;
(6) compounds I according to (1) to (5) wherein $A_4$ is a straight-chain alkylene bridge, especially ethylene, propylene or butylene, more especially ethylene or propylene, very especially propylene;
(7) compounds I according to (1) to (6) wherein Q is oxygen;
(8) compounds I according to (1) to (7) wherein Y is oxygen;
(9) compounds I according to (1) to (8) wherein $R_1$ and $R_2$ are bromine or chlorine, especially chlorine;
(10) compounds I according to (1) to (9) wherein m is 0;

(11) compounds I according to (1) to (10) wherein $R_4$ is halogen, especially chlorine, and k is 2 or 0;

(12) compounds I according to (1) to (11) wherein D is CH;

(13) compounds I according to (1) to (12), wherein Het is 5-oxo-2-($C_1$-$C_6$alkyl)-3,4-diaza-1-thia-cyclopent-2-en-4-yl, 5-oxo-2-($C_1$-$C_6$alkyl)-3,4-diaza-1-oxa-cyclopent-2-en-4-yl, 5-oxo-2-(halo-$C_1$-$C_6$alkyl)-3,4-diaza-1-oxa-cyclopent-2-en-4-yl, 5-oxo-1-($C_1$-$C_6$alkyl)-2-($C_1$-$C_6$alkyl)-1,3,4-triaza-cyclopent-2-en-4-yl, 5-oxo-1-(halo-$C_1$-$C_6$alkyl)-2-($C_1$-$C_6$alkyl)-1,3,4-triaza-cyclopent-2-en-4-yl, 5-oxo-1-($C_1$-$C_6$alkyl)-1,2,3,4-tetraaza-cyclopent-2-en-4-yl, 4-halo-5-halo-6-oxo-1,2-diaza-cyclohexa-2,4-dien-1-yl, 3-oxo-4-($C_1$-$C_6$alkyl)-5-(halo-$C_1$-$C_6$alkyl)-1,4-diaza-cyclohexa-1,5-dien-2-yl or 6-oxo-1-($C_1$-$C_6$alkyl)-2-($C_1$-$C_6$alkyl)-1,3-diaza-cyclohexa-2,4-dien-5-yl, especially 5-oxo-2-($C_1$-$C_6$alkyl)-3,4-diaza-1-thia-cyclopent-2-en-4-yl, 5-oxo-2-($C_1$-$C_6$alkyl)-3,4-diaza-1-oxa-cyclopent-2-en-4-yl or 5-oxo-2-(halo-$C_1$-$C_6$alkyl)-3,4-diaza-1-oxa-cyclopent-2-en-4-yl.

In the context of the invention, special preference is given to the compounds of formula I mentioned in Examples P1 and P2.

The invention relates also to a process for the preparation of compounds of formula I or, where applicable, E/Z isomers, mixtures of E/Z isomers and/or tautomers thereof, in each case in free form or in salt form, which process comprises, for example, (a) for the preparation of a compound I wherein W is O, $NR_5$, S, —C(=O)—O— or —C(=O)—$NR_6$—, reacting a compound of formula

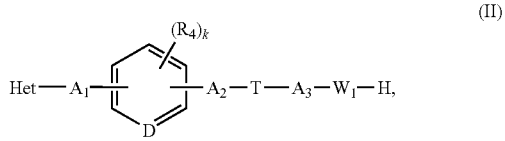

(II)

wherein $W_1$ is O, $NR_5$, S, —C(=O)—O— or —C(=O)—$NR_6$— and $R_5$, $R_6$, Het, $A_1$, $A_2$, $A_3$, D, T, $R_4$ and k are as defined for formula I under (1), preferably in the presence of a base, with a compound of formula

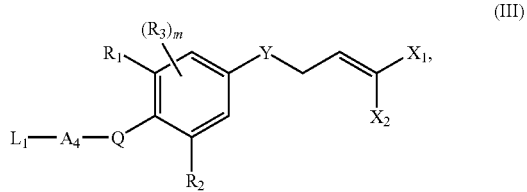

(III)

wherein $A_4$, $R_1$, $R_2$, $R_3$, Q, $X_1$, $X_2$, Y and m are as defined for formula I under (1) and $L_1$ is a leaving group or, (b) for the preparation of a compound I wherein Q is O, $NR_5$ or S, reacting a compound of formula

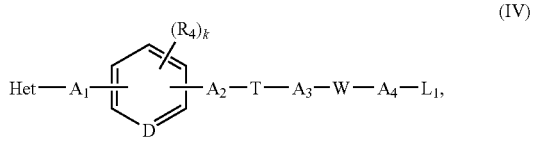

(IV)

wherein Het, $A_1$, $A_2$, $A_3$, $A_4$, D, T, W, $R_4$ and k are as defined for formula I under (1) and $L_1$ is a leaving group, preferably in the presence of a base, with a compound of formula

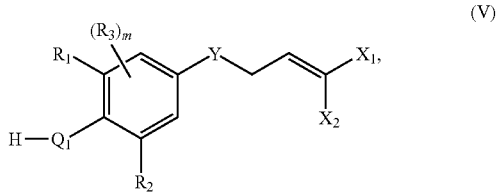

(V)

wherein $Q_1$ is O, $NR_5$ or S and $R_5$, $R_1$, $R_2$, $R_3$, $X_1$, $X_2$, Y and m are as defined for formula I under (1), and/or converting a compound of formula I or a tautomer thereof, in each case in free form or in salt form, into a different compound of formula I or a tautomer thereof, separating a mixture of isomers obtainable according to the process and isolating the desired isomer, and/or converting a free compound of formula I or a tautomer thereof into a salt, or a salt of a compound of formula I or of a tautomer thereof into the free compound of formula I or a tautomer thereof or into a different salt.

The reactions described hereinabove and hereinbelow are carried out in a manner known per se, for example in the absence or usually in the presence of a suitable solvent or diluent or a mixture thereof, the reactions being carried out, as required, with cooling, at room temperature or with heating, for example in a temperature range of from about −80° C. to the boiling point of the reaction mixture, preferably from about −20° C. to about +150° C., and, if necessary, in a closed vessel, under pressure, in an inert gas atmosphere and/or under anhydrous conditions. Especially advantageous reaction conditions can be found in the Examples.

A leaving group $L_1$ is to be understood hereinabove and hereinbelow as being any removable group customarily considered for chemical reactions, such as are known to the person skilled in the art, especially OH, a halogen such as fluorine, chlorine, bromine or iodine, —O—Si($C_1$-$C_8$alkyl)$_3$, —O-aryl, —S—($C_1$-$C_8$alkyl), —S-aryl, —O—S(=O)$_2$U, —S(=O)U or —S(=O)$_2$U, wherein U is unsubstituted or substituted $C_1$-$C_8$alkyl, $C_2$-$C_8$alkenyl, $C_2$-$C_8$alkynyl, unsubstituted or substituted aryl or unsubstituted or substituted benzyl. Especially preferred leaving groups are chlorine or bromine, mesylate, triflate, tosylate, especially chlorine; and chloride or bromide, especially chloride.

Process (a)

The reaction is carried out, for example, in an ether or in an amide, such as N,N-dimethylformamide or N-methylpyrrolidone, and at from 0 to 150° C. The base used may be, for example, sodium hydride.

Process (b)

Preference is given to proceeding in an ether, dimethylformamide, dimethyl acetamide or N-methylpyrrolidone, at a temperature of from 0° C. to 150° C., preferably from 20° C. to 80° C., with the addition of a base, such as potassium or sodium carbonate. Alternatively, a coupling reagent, for example azodicarboxylic acid diethyl or diisopropyl ester and triphenylphospine, may be used.

Compounds of formula (I) obtainable in accordance with the process or by another method can be converted in a manner known per se into different compounds of formula (I) by replacing one or more substituents of the starting compound of formula (I) by (an) other substituent(s) according to the invention in customary manner.

Depending upon the reaction conditions and starting materials selected as suitable in each case, it is possible in a reaction step to replace only one substituent by another substituent according to the invention or it is possible in the same reaction step to replace a plurality of substituents by other substituents according to the invention.

Salts of compounds of formula (I) can be prepared in a manner known per se. For example, salts of compounds of formula (I) with bases are obtained by treatment of the free compounds with a suitable base or a suitable ion exchange reagent.

Salts of compounds of formula (I) can be converted in customary manner into the free compounds of formula (I), for example by treatment with a suitable acid or a suitable ion exchange reagent.

Salts of compounds of formula (I) can be converted into different salts of a compound of formula (I) in a manner known per se.

The compounds of formula (I) in free form or in salt form may be in the form of one of the possible isomers or in the form of a mixture thereof, for example depending upon the number of asymmetric carbon atoms present in the molecule and the absolute and relative configuration thereof, and/or, depending upon the configuration of non-aromatic double bonds present in the molecule, may be in the form of pure isomers, such as antipodes and/or diastereoisomers, or in the form of mixtures of isomers, such as mixtures of enantiomers, for example racemates, mixtures of diastereoisomers or mixtures of racemates. The invention relates both to the pure isomers and to all possible mixtures of isomers and this is to be understood accordingly hereinabove and hereinbelow, even when stereochemical details are not specifically mentioned in each case.

Mixtures of diastereoisomers, mixtures of racemates and mixtures of double-bond isomers of compounds of formula (I) in free form or in salt form obtainable in accordance with the process—depending upon the starting materials and procedures chosen—or by other means can be separated into the pure diastereoisomers, racemates or double bond isomers in known manner on the basis of the physico-chemical differences between the constituents, for example by fractional crystallisation, distillation and/or chromatography.

Mixtures of enantiomers, such as racemates, so obtainable can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, or via the formation of inclusion compounds, for example using chiral crown ethers, in which case only one enantiomer is complexed, or by conversion into diastereoisomeric salts and separation of the mixture of diastereoisomers thereby obtained, for example on the basis of their different solubilities by fractional crystallisation, into the diastereoisomers from which the desired enantiomer can be freed by the action of suitable agents.

Pure diastereoisomers and enantiomers can be obtained not only by separation of corresponding mixtures of isomers but also, according to the invention, by generally known methods of diastereoselective or enantioselective synthesis, for example by carrying out the process according to the invention with starting materials that have appropriate stereochemistry.

It is advantageous to isolate or synthesise whichever isomer, for example enantiomer or diastereoisomer, or mixture of isomers, for example mixture of enantiomers or of diastereoisomers, is biologically more active, insofar as the individual components have different biological activities.

The compounds of formula (I) in free form or in salt form may also be obtained in the form of their hydrates and/or may include other solvents, for example solvents which may optionally have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative or a salt and/or its racemates or antipodes, or, especially, is formed under the reaction conditions.

In the process of the present invention it is preferable to use those starting materials and intermediates, in each case in free form or in salt form, which result in the compounds of formula (I) described hereinabove as being especially valuable, or salts thereof.

The invention relates especially to the preparation processes described in Examples P1 and P2.

The invention relates likewise to the intermediates of formulae (II) to (V), and, where applicable, possible E/Z isomers, mixtures of E/Z isomers and/or tautomers thereof, in each case in free form or in salt form, insofar as they are novel. The same preferences apply to those compounds as to the compounds of formula (I).

In the area of pest control, the compounds of formula (I) according to the invention are active ingredients exhibiting valuable preventive and/or curative activity with a very advantageous biocidal spectrum, even at low rates of concentration, while being well tolerated by warm-blooded organisms, fish and plants. The active ingredients according to the invention are effective against all or individual development stages of normally sensitive animal pests, but also of resistant animal pests, such as insects and representatives of the order Acarina. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The mentioned animal pests include, for example, those mentioned in European Patent Application EP-A-736 252, page 5, line 55, to page 6, line 55. The pests mentioned therein are accordingly included in the subject-matter of the present invention by reference. The active ingredients according to the invention are especially suitable for controlling *Boophilus microplus*, *Nilaparvata lugens* and *Tetranychus urticae*, preferably for controlling those pests in crops of vegetables, fruit and rice.

The active ingredients according to the invention can be used to control, i.e. to inhibit or destroy, pests of the mentioned type occurring especially on plants, more especially on useful plants and ornamentals in agriculture, in horticulture and in forestry, or on parts of such plants, such as the fruits, blossoms, leaves, stems, tubers or roots, while in some cases parts of plants that grow later are still protected against those pests.

Target crops are especially cereals, e.g. wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the active ingredients according to the invention are the protection of stored goods and storerooms and the protection of raw materials, and also in the hygiene sector, especially the protection of domestic animals and productive livestock against pests of the mentioned type.

The invention accordingly relates also to pesticidal compositions, such as emulsifiable concentrates, suspension concentrates, directly sprayable or dilutable solutions, coatable pastes, dilute emulsions, sprayable powders, soluble powders, dispersible powders, wettable powders, dusts, granules or encapsulations in polymer substances, that comprise at least one of the active ingredients of the invention, the choice of formulation being made in accordance with the intended objectives and the prevailing circumstances.

The active ingredient is used in those compositions in pure form: a solid active ingredient, for example, in a specific particle size, or preferably together with at least one of the adjuvants customary in formulation technology, such as extenders, for example solvents or solid carriers, or surface-active compounds (surfactants).

As formulation adjuvants there are used, for example, solid carriers, solvents, stabilisers, "slow release" adjuvants, dyes and optionally surface-active substances (surfactants). Suitable carriers and adjuvants include all those substances customarily used in the case of crop protection compositions, especially slug and snail control agents. Suitable adjuvants, such as solvents, solid carriers, surface-active compounds, non-ionic surfactants, cationic surfactants, anionic surfactants and other adjuvants in the compositions used according to the invention, include e.g. those described in EP-A-736 252, which are included in the subject-matter of the present invention by reference.

The compositions generally comprise from 0.1 to 99%, especially from 0.1 to 95%, of active ingredient and from 1 to 99.9%, especially from 5 to 99.9%, of at least one solid or liquid adjuvant, it generally being possible for from 0 to 25%, especially from 0.1 to 20%, of the compositions to consist of surfactants (%=% by weight). Whereas commercial products will preferably be formulated as concentrates, the end user will normally employ dilute formulations, which have much lower active ingredient concentrations. Preferred compositions have especially the following compositions (%=% by weight):

Emulsifiable Concentrates:

| active ingredient: | 1 to 95%, preferably 5 to 20% |
| surfactant: | 1 to 30%, preferably 10 to 20% |
| solvent: | 5 to 98%, preferably 70 to 85% |

Dusts:

| active ingredient: | 0.1 to 10%, preferably 0.1 to 1% |
| solid carrier: | 99.9 to 90%, preferably 99.9 to 99% |

Suspension Concentrates:

| active ingredient: | 5 to 75%, preferably 10 to 50% |
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
| surfactant: | 0.5 to 20%, preferably 1 to 15% |
| solid carrier: | 5 to 99%, preferably 15 to 98% |

Granules:

| active ingredient: | 0.5 to 30%, preferably 3 to 15% |
| solid carrier: | 99.5 to 70%, preferably 97 to 85% |

The action of the compounds according to the invention and of compositions comprising them against animal pests can be significantly broadened and adapted to prevailing circumstances by the addition of other insecticides, acaricides or nematicides. Examples of suitable additives include representatives of the following classes of active ingredients: organophosphorus compounds, nitrophenols and derivatives, formamidines, ureas, carbamates, pyrethroids, chlorinated hydrocarbons, neonicotinoids and *Bacillus thuringiensis* preparations.

Especially suitable mixing partners are, for example: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodofenphos; kinoprene; lufenuron; methacriphos; methidathion; monocrotophos; phosphamidon; profenofos; diofenolan; a compound obtainable from the *Bacillus thuringiensis* strain GC91 or from the strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; avermectin B1 (abamectin); emamectin; emamectin benzoate; spinosad; a plant extract that is active against insects; a preparation that contains nematodes and that is active against insects; a preparation obtainable from *Bacillus subtilis*; a preparation that contains fungi and that is active against insects; a preparation that contains viruses and that is active against insects; chlorfenapyr; acephate; acrinathrin; alanycarb; alphamethrin; amitraz; Az 60541; azinphos A; azinphos M; azocyclotin; bendiocarb; bensultap; beta-cyfluthrin; BPMC; brofenprox; bromophos A; bufencarb; butocarboxim; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; Nc 184; omethoate; oxamyl; oxydemeton M; oxydeprofos; permethrin; phenthoate; phorate; phosmet; phoxim; pirimiphos M; pirimiphos E; promecarb; propaphos; prothiofos; prothoate; pyrachlophos; pyridaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium anisopliae*; very especially fipronil, thiamethoxam or lambda-cyhalothrin.

The compositions according to the invention may also comprise further solid or liquid adjuvants, such as stabilisers, e.g. vegetable oils and epoxidised vegetable oils (e.g. epoxidised coconut oil, rapeseed oil or soybean oil), antifoams, e.g. silicone oil, preservatives, viscosity regulators, binders and/or tackifiers, and also fertilisers or other active ingredients for obtaining special effects, e.g. acaricides, bactericides, fungicides, nematicides, molluscicides or selective herbicides.

The compositions according to the invention are prepared in known manner, in the absence of adjuvants, for example by grinding, sieving and/or compressing a solid active ingredient or mixture of active ingredients, for example to a specific particle size, or in the presence of at least one adjuvant, for example by intimately mixing and/or grinding the active ingredient or mixture of active ingredients with the adjuvant(s). The invention relates also to those processes for the preparation of the compositions according to the invention and to the use of the compounds of formula (I) in the preparation of those compositions.

The invention relates also to the methods of application of the compositions, i.e. the methods of controlling pests of the mentioned type, such as spraying, atomising, dusting, coating, dressing, scattering or pouring, which are selected in accordance with the intended objectives and prevailing circumstances, and to the use of the compositions for controlling pests of the mentioned type. Typical application concentrations are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the foliage of the plants (foliar application), the application frequency and the rate of application depending on the risk of infestation by the pest in question. However, the active ingredient can also penetrate the plants through the roots (systemic action) if the locus of the plants is impregnated with a liquid formulation or if the active ingredient is incorporated in solid form into the locus of the plants, for example into the soil, e.g. in granular form (soil application). In paddy rice crops, such granules may be applied in metered amounts to the flooded rice field.

The compositions according to the invention are also suitable for protecting plant propagation material, including genetically modified propagation material, e.g. seed material, such as fruit, tubers or grains, or plant cuttings, from animal pests. The propagation material can be treated with the formulation before planting: seed material, for example, can be dressed before being sown. The compounds according to the invention can also be applied to grains (coating), either by impregnating the grains with a liquid formulation or by coating them with a solid formulation. The formulation can also be applied to the planting site when the propagation material is being planted, for example to the seed furrow during sowing. The invention relates also to those methods of treating plant propagation material and to the plant propagation material so treated.

The following Examples serve to illustrate the invention. They do not limit the invention. Temperatures are in degrees Celsius; "m.p." denotes the melting point of the compound in question.

PREPARATION EXAMPLES

Example P1

Preparation of Compound No. 1.4

The free form of the hydrazine is freed from the hydrochloride of 4-methoxyphenyl-hydrazine by treatment with a base. The free 4-methoxyphenylhydrazine is isolated and is used in that form for the further reaction.

To a mixture of 50 ml of dichloromethane and 2.76 g of free 4-methoxyphenyl-hydrazine there are added first 2.2 g of triethylamine and then, dropwise, at a temperature of from 0° to 5°, 2.65 g of pivaloyl chloride. The reaction mixture is stirred for 12 hours at room temperature and then discharged into water. The aqueous mixture is extracted with dichloromethane, the extract is concentrated and the residue is recrystallised from toluene/pentane, yielding N-(4-methoxyphenyl)-N'-pivaloyl-hydrazine which melts at from 126° to 127°.

12 ml of a (20%) solution of phosgene in toluene are added dropwise, at room temperature, to a mixture of 50 ml of toluene, 0.1 ml of N,N-dimethylformamide and 2.3 g of N-(4-methoxyphenyl)-N'-pivaloyl-hydrazine. The reaction mixture is stirred at reflux for 7 hours and then concentrated. After purification of the residue on silica gel, 1-methoxy-4-(5-oxo-2-tert-butyl-3,4-diaza-1-oxa-cyclopent-2-en-4-yl)-benzene is obtained in the form of a colourless oil.

3.5 g of boron tribromide are slowly added dropwise, at −60°, to a mixture of 70 ml of dichloromethane and 1.5 g of 1-methoxy-4-(5-oxo-2-tert-butyl-3,4-diaza-1-oxa-cyclopent-2-en-4-yl)-benzene. The reaction mixture is stirred at room temperature for 12 hours and then discharged onto ice/water. The aqueous mixture is extracted with dichloromethane, the extract is washed with water and concentrated and the residue is recrystallised from toluene/pentane, yielding 1-hydroxy-4-(5-oxo-2-tert-butyl-3,4-diaza-1-oxa-cyclopent-2-en-4-yl)-benzene, which melts at from 170° to 172°.

A mixture of 30 ml of acetone, 151.5 mg of 1-hydroxy-4-(5-oxo-2-tert-butyl-3,4-diaza-1-oxa-cyclopent-2-en-4-yl)- benzene, 74.2 mg of potassium carbonate and 204.5 mg of 4-(3-bromoprop-1-yloxy)-3,5-dichloro-1-(3,3-dichloro-prop-2-en-1-yloxy)-benzene is stirred at reflux for 12 hours and then concentrated. The residue is taken up in ethyl acetate and the mixture is washed with hydrochloric acid (0.1N) and water and concentrated. After purification of the residue on silica gel, the title compound (compound No. 1.4) is obtained in the form of a colourless oil.

Example P2

The other compounds listed in Table 1 can be prepared in a manner analogous to that described in Example P1.

TABLE 1

General structure:

R_2, R_3 substituents on a benzene ring linked via –O–[CH_2]_n–O– to a 2,6-dichloro-4-(3,3-dichloroprop-2-en-1-yloxy)phenyl group; R_1 on the first benzene ring.

| Compound No. | $R_1$ | $R_2$ | $R_3$ | n | Physical data |
|---|---|---|---|---|---|
| 1.1 | H | 5-methyl-2-oxo-1,3,4-thiadiazol-2(3H)-yl (H_3C-thiadiazolinone) | H | 1 | resin |
| 1.2 | H | 5-isopropyl-3-methyl-1,3,4-oxadiazol-2(3H)-one-yl ((H_3C)_2HC-) | H | 1 | m.p.: 57–59° |
| 1.3 | H | 5-trifluoromethyl-3-methyl-1,3,4-oxadiazol-2(3H)-one-yl (F_3C-) | H | 1 | oil |
| 1.4 | H | 5-tert-butyl-3-methyl-1,3,4-oxadiazol-2(3H)-one-yl ((H_3C)_3C-) | H | 1 | oil |
| 1.5 | Cl | 5-tert-butyl-3-methyl-1,3,4-oxadiazol-2(3H)-one-yl ((H_3C)_3C-) | Cl | 1 | m.p.: 85–87° |
| 1.6 | H | 3-methyl-5-methyl-4-isopropyl-1,2,4-triazol-3(2H)-one-yl | H | 1 | m.p.: 90–91° |
| 1.7 | H | 3-methyl-5-methyl-4-difluoromethyl-1,2,4-triazol-3(2H)-one-yl | H | 1 | m.p.: 85–86° |
| 1.8 | H | 3-methyl-4-methyl-5-tert-butyl-1,2,4-triazol-3(2H)-one-yl | H | 1 | |
| 1.9 | H | 5-tert-butyl-2-methyl-4-isopropyl-1,2,4-triazol-3(2H)-one-yl | H | 1 | |
| 1.10 | H | 5-tert-butyl-2-methyl-4-difluoromethyl-1,2,4-triazol-3(2H)-one-yl | H | 1 | |
| 1.11 | H | 1,4-dimethyl-1,2,3,4-tetrazol-5(4H)-one-yl | H | 1 | m.p. 80–82° |
| 1.12 | H | 1-ethyl-4-methyl-1,2,3,4-tetrazol-5(4H)-one-yl | H | 1 | m.p. 63–65° |
| 1.13 | H | 1-isopropyl-4-methyl-1,2,3,4-tetrazol-5(4H)-one-yl | H | 1 | oil |

TABLE 1-continued
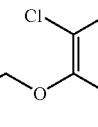
| Compound No. | R₁ | R₂ | R₃ | n | Physical data |
|---|---|---|---|---|---|
| 1.14 | H | 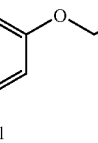 | H | 1 | |
| 1.15 | H | 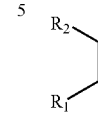 | H | 1 | |
| 1.16 | H | 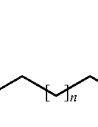 | H | 1 | |
| 1.17 | H | 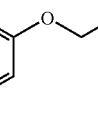 | H | 0 | |
| 1.18 | H |  | H | 0 | |
| 1.19 | H |  | H | 0 | |
| 1.20 | H | 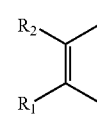 | H | 0 | |
| 1.21 | Cl | 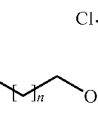 | Cl | 0 | |
| 1.22 | H | 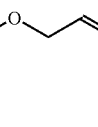 | H | 0 | |
| 1.23 | H |  | H | 0 | |
| 1.24 | H |  | H | 0 | |
| 1.25 | H | | H | 0 | |
| 1.26 | H | | H | 0 | |
| 1.27 | H | | H | 0 | |

TABLE 1-continued
| Compound No. | R₁ | R₂ | R₃ | n | Physical data |
|---|---|---|---|---|---|
| 1.28 | H | 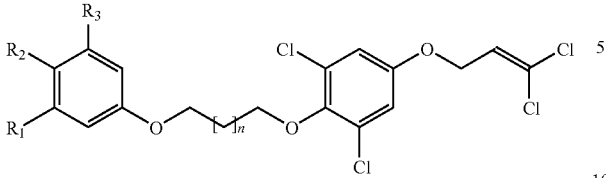 | H | 0 | |
| 1.29 | H | 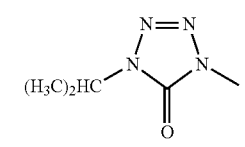 | H | 0 | |
| 1.30 | H | 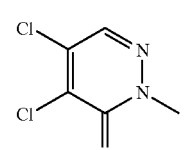 | H | 0 | |
| 1.31 | H |  | H | 0 | |
| 1.32 | H | 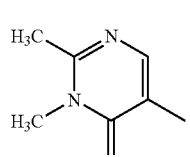 | H | 0 | |
| 1.33 | H | 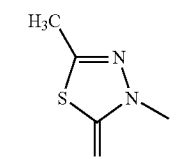 | H | 2 | |
| 1.34 | H | 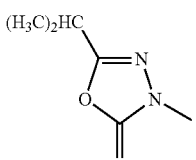 | H | 2 | |
| 1.35 | H |  | H | 2 | |
| 1.36 | H | 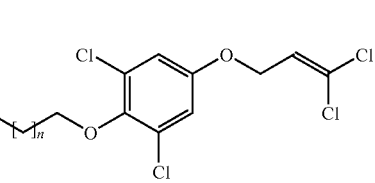 | H | 2 | |
| 1.37 | Cl | 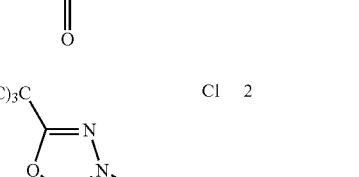 | Cl | 2 | |
| 1.38 | H | 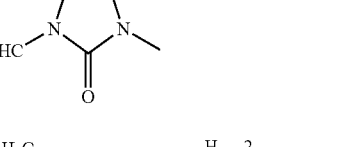 | H | 2 | |
| 1.39 | H | 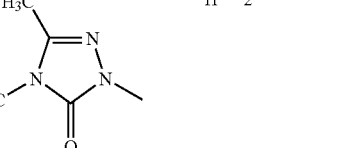 | H | 2 | |
| 1.40 | H | 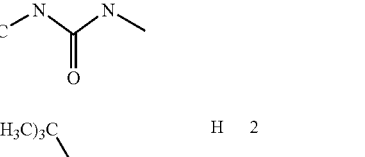 | H | 2 | |
| 1.41 | H | 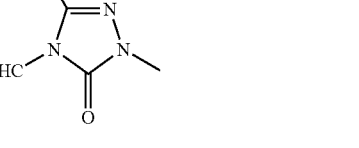 | H | 2 | |
| 1.42 | H | 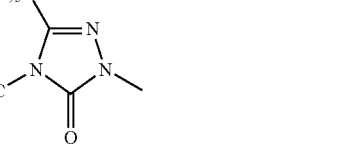 | H | 2 | |

TABLE 1-continued
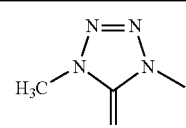
| Compound No. | R₁ | R₂ | R₃ | n | Physical data |
|---|---|---|---|---|---|
| 1.43 | H | 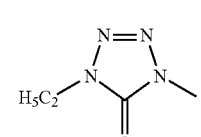 | H | 2 | |
| 1.44 | H | 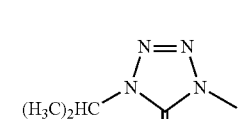 | H | 2 | |
| 1.45 | H | 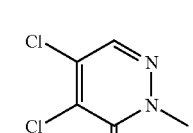 | H | 2 | |
| 1.46 | H | 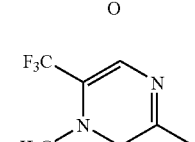 | H | 2 | |
| 1.47 | H | 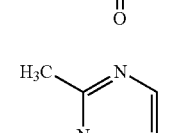 | H | 2 | |
| 1.48 | H | 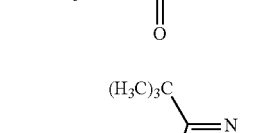 | H | 2 | |
| 1.49 | H | 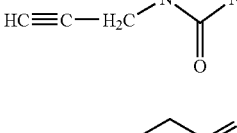 | H | 1 | resin |
| 1.50 | H | (H₃C)₂HC group with oxazine | H | 1 | resin |
| 1.51 | H | H₃CS pyridazinone with Cl | H | 1 | resin |
| 1.52 | H | H₅C₂ triazolone | H | 1 | oil |
| 1.53 | H | (H₃C)₂HC triazolone | H | 1 | oil |
| 1.54 | H | H₅C₂ oxadiazolone | H | 1 | m.p.: 78–81° |
| 1.55 | H | (H₃C)₃C oxadiazolone | H | 1 | oil |
| 1.56 | H | (H₃C)₂HC oxadiazolone | H | 1 | m.p.: 99–103° |
| 1.57 | H | (H₃C)₂HC triazolone with C₂H₅ | H | 1 | resin |
| 1.58 | H | F₂HC triazolone | H | 1 | m.p.: 78–80° |

TABLE 1-continued

[Structure: R₃, R₂, R₁ substituted phenyl-O-[CH₂]ₙ-O-phenyl(Cl, Cl)-O-CH₂-CH=CCl₂ with Cl substituent]

| Compound No. | R₁ | R₂ | R₃ | n | Physical data |
|---|---|---|---|---|---|
| 1.59 | H | [imidazolidine-2,4-dione with H₅C₂-N and N-CH₂-] | H | 1 | oil |

Formulation Examples (%=percent by weight)

Example F1: Emulsifiable concentrates

|  | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Mixing finely ground active ingredient and additives gives an emulsifiable concentrate which yields emulsions of the desired concentration on dilution with water.

Example F2: Solutions

|  | a) | b) | c) | d) |
|---|---|---|---|---|
| active ingredient | 80% | 10% | 5% | 95% |
| ethylene glycol monomethyl ether | 20% | — | — | — |
| polyethylene glycol (MW 400) | — | 70% | — | — |
| N-methylpyrrolid-2-one | — | 20% | — | — |
| epoxidised coconut oil | — | — | 1% | 5% |
| benzine (boiling range: 160-190°) | — | — | 94% | — |

Mixing finely ground active ingredient and additives gives a solution suitable for use in the form of microdrops.

Example F3: Granules

|  | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture and the solvent is evaporated off in vacuo.

BIOLOGICAL EXAMPLES

Example B1

Action Against *Heliothis virescens*

Young soybean plants are sprayed with an aqueous emulsion spray mixture comprising 400 ppm of active ingredient. After the spray-coating has dried, the soybean plants are populated with 10 caterpillars of *Heliothis virescens* in the first stage and placed in a plastics container. Evaluation is made 6 days later. The percentage reduction in population and the percentage reduction in feeding damage (% activity) are determined by comparing the number of dead caterpillars and the feeding damage on the treated plants with that on the untreated plants.

The compounds of Table 1 exhibit good activity against *Heliothis virescens* in this test. In particular, compounds 1.1, 1.2, 1.3, 1.4, 1.5 and 1.49 to 1.59 exhibit an activity of more than 80%.

Example B2

Action Against *Plutella xylostella*

Young cabbage plants are sprayed with an aqueous emulsion spray mixture comprising 400 ppm of active ingredient. After the spray-coating has dried, the cabbage plants are populated with 10 caterpillars of *Plutella xylostella* in the third stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

The compounds of Table 1 exhibit good activity against *Plutella xylostella* in this test. In particular, compounds 1.1, 1.2, 1.3, 1.4, 1.5 and 1.49 to 1.59 exhibit an activity of more than 80%.

Example B3

Action Against *Spodoptera littoralis*

Young soybean plants are sprayed with an aqueous emulsion spray mixture comprising 400 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants. The compounds of Table 1 exhibit good activity against *Spodoptera littoralis* in this test. In particular, compounds 1.1, 1.2, 1.3, 1.4, 1.5 and 1.49 to 1.59 exhibit an activity of more than 80%.

What is claimed is:

1. A compound of formula (I)

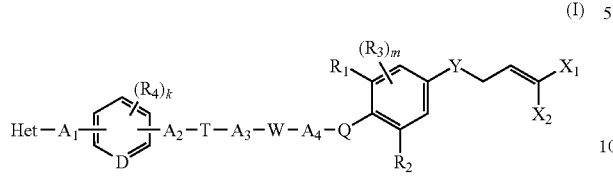

wherein:
Het is

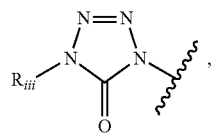

wherein $R_{iii}$ is $C_1$-$C_3$alkyl or halo-$C_1$-$C_3$alkyl;

$A_1$, $A_2$, and $A_3$ are each independently of the others a bond or a $C_1$-$C_6$alkylene bridge which is unsubstituted or substituted from one to six times by, each independently of the other(s), $C_3$-$C_8$cycloalkyl, $C_3$-$C_8$cycloalkyl-$C_1$-$C_6$alkyl, or halo-$C_1$-$C_3$alkyl;

$A_4$ is a $C_1$-$C_6$alkylene bridge which is unsubstituted or substituted from one to six times by, each independently of the other (s), $C_3$-$C_8$cycloalkyl, $C_3$-$C_8$cycloalkyl-$C_1$-$C_6$alkyl, or halo-$C_1$-$C_3$alkyl;

D is CH or N;

W is O, $NR_5$, S, S(=O), S(=O)$_2$, —C(=O)—O—, —O—C(=O)—, —O(O)—$NR_6$—, or —$NR_6$—C(=O)—;

T is a bond, O, NH, $NR_5$, S, S(O), S(O)$_2$, —O(O)—O—, —O—O(O)—, —C(=O)—$NR_6$—, or —$NR_6$—C(O)—;

Q is O, $NR_5$, S, S(=O), or S(=O)$_2$;

Y is O, $NR_5$, S, S(=O), or S(=O)$_2$;

$X_1$ and $X_2$ are each independently of the other fluorine, chlorine, or bromine;

$R_1$ and $R_2$ are each independently of the other H, halogen, ON, nitro, $C_1$-$C_6$alkyl, halo-$C_1$-$C_6$alkyl, $C_1$-$C_6$alkylcarbonyl, $C_2$-$C_6$alkenyl, halo-$C_2$-$C_6$alkenyl, $C_2$-$C_6$alkynyl, $C_1$-$C_6$alkoxy, halo-$C_1$-$C_6$alkoxy, $C_2$-$C_6$alkenyloxy, halo-$C_2$-$C_6$alkenyloxy, $C_3$-$C_6$alkynyloxy, $C_1$-$C_6$alkoxycarbonyl, or halo-$C_3$-$C_6$alkynyloxy;

$R_3$ is halogen, CN, nitro, $C_1$-$C_6$alkyl, halo-$C_1$-$C_6$alkyl, $C_1$-$C_6$alkylcarbonyl, $C_2$-$C_6$alkenyl, halo-$C_2$-$C_6$alkenyl, $C_2$-$C_6$alkynyl, $C_1$-$C_6$alkoxy, halo-$C_1$-$C_6$alkoxy, $C_2$-$C_6$alkenyloxy, halo-$C_2$-$C_6$alkenyloxy, $C_3$-$C_6$alkynyloxy, $C_1$-$C_6$alkoxycarbonyl, or halo-$C_3$-$C_6$alkynyloxy, the two $R_3$ substituents being identical or different when m is 2;

$R_4$ is halogen, CN, nitro, $C_1$-$C_6$alkyl, halo-$C_1$-$C_6$alkyl, $C_1$-$C_6$alkylcarbonyl, $C_2$-$C_6$alkenyl, halo-$C_2$-$C_6$alkenyl, $C_2$-$C_6$alkynyl, $C_1$-$C_6$alkoxy, halo-$C_1$-$C_6$alkoxy, $C_2$-$C_6$alkenyloxy, halo-$C_2$-$C_6$alkenyloxy, $C_3$-$C_6$alkynyloxy, $C_1$-$C_6$alkoxycarbonyl, or halo-$C_3$-$C_6$alkynyloxy, the $R_4$ substituents being identical or different when k is greater than 1;

$R_5$ is H, $C_1$-$C_6$alkyl, halo-$C_1$-$C_3$alkyl, halo-$C_1$-$C_3$alkylcarbonyl, $C_1$-$C_6$alkoxyalkyl, $C_1$-$C_6$alkylcarbonyl, or $C_3$-$C_8$cycloalkyl;

$R_6$ is H, $C_1$-$C_6$alkyl, halo-$C_1$-$C_3$alkyl, halo-$C_1$-$C_3$alkylcarbonyl, $C_1$-$C_6$alkoxyalkyl, $C_1$-$C_6$alkylcarbonyl, or $C_3$-$C_8$cycloalkyl;

k is 0, 1, 2, or 3, when D is N; or k is 0, 1, 2, 3, or 4, when D is CH; and m is 0, 1, or 2, or, where applicable, possible E/Z isomers, mixtures of E/Z isomers, or tautomers thereof, in each case in free form or in salt form.

2. A compound according to claim 1 in free form.

3. A compound according to claim 1, wherein $X_1$ and $X_2$ are chlorine or bromine.

4. A compound according to claim 1, wherein $A_1$ is a bond.

5. A compound according to claim 1, wherein the group $A_2$-T-$A_3$ is a bond.

6. A compound according to claim 1, wherein W is —O—, —O(=O)O—, or —C(=O)NH—.

7. A compound according to claim 1, wherein $A_4$ is a straight-chain alkylene bridge.

8. A compound according to claim 1, wherein Q is oxygen.

9. A compound according to claim 1, wherein Y is oxygen.

10. A compound according to claim 1, wherein $R_1$ and $R_2$ are bromine or chlorine.

11. A compound according to claim 1, wherein m is 0.

12. A compound according to claim 1, wherein $R_4$ is halogen and k is 2 or 0.

13. A compound according to claim 1, wherein D is CH.

14. A pesticidal composition comprising as active ingredient at least one compound according to claim 1, in free form or in agrochemically usable salt form, and at least one adjuvant.

15. A process for the preparation of a composition as described in claim 14, which comprises intimately mixing the active ingredient with the adjuvants.

16. A method of controlling one or more pests selected from the group consisting of insects and representatives of the order Acarina, which comprises applying a composition as described in claim 14 to the pests or to the locus thereof.

* * * * *